United States Patent [19]

Odle

[11] Patent Number: 4,921,970

[45] Date of Patent: May 1, 1990

[54] NITRATION REACTIONS WITH ACID ANHYDRIDE PROMOTERS

[75] Inventor: Roy R. Odle, Schuylerville, N.Y.

[73] Assignee: General Electric Company, Pittsfield, Mass.

[21] Appl. No.: 12,318

[22] Filed: Feb. 9, 1987

Related U.S. Application Data

[63] Continuation of Ser. No. 567,485, Jan. 1, 1984, abandoned.

[51] Int. Cl.$^5$ ............................................. C07D 209/50
[52] U.S. Cl. ................................................... 548/480
[58] Field of Search ...................... 548/480; 562/434; 549/243

[56] References Cited

U.S. PATENT DOCUMENTS

| | | | |
|---|---|---|---|
| 3,397,229 | 8/1968 | Welch | 260/515 |
| 3,415,876 | 12/1978 | Boonstra et al. | 260/515 |
| 3,868,389 | 2/1975 | Takekoshi | 548/462 |
| 3,887,588 | 6/1975 | Cook et al. | 549/243 |
| 3,933,852 | 1/1976 | Cook et al. | 548/481 |
| 3,981,933 | 9/1976 | Cook et al. | 548/481 |
| 4,036,838 | 7/1977 | Vogel et al. | 260/515 |
| 4,064,147 | 12/1977 | Thelen et al. | 260/369 |
| 4,112,005 | 9/1978 | Thiem et al. | 564/146 |

FOREIGN PATENT DOCUMENTS

| | | |
|---|---|---|
| 108604 | 5/1984 | European Pat. Off. |
| 1393312 | 2/1965 | France. |

OTHER PUBLICATIONS

A. Murthy, "Practical Nitration and Amination Technology" Conference Paper Excerpts (Dec. 1985).
E. Muller, Meth. der Organischen Chemie, 1971.
Hughes et al, "Kinetics and Mechanism of Aromatic Nitration, Part II", pp. 2400–2440 (1949).
K. Schofield, "Aromatic Nitration", Cambridge Univ. Press, pp. 23–43 (1980).
M. Astle, "Industrial Organic Nitrogen Compounds", Reinhold Publishing Corp., pp. 314–344 (1961), pp. 459 (1943).
C. Noller, "Chem. of Organic Compounds", Sunders Co., pp. 439–455 (1958).
A. Ponomarenko, "Synthesis of Monochlorophthalic Anhydrides from Mononitrophthalic Anhydrides", Zhur. Obsche: Khim (J. Gené. Chem.), pp. 20, 469–471 (1948).
T. Kameo et al, Chem. Abstracts 79:104832v (1973).
Stamicarbon N. V., Chem. Abstracts 68:95548a (1968).
B. Enoksson et al, Chem. Abstracts 96:201967b (1982).
Hoggett et al., *Nitration and Aromatic Reactivity*, Cambridge University Press, pp. 6–7 and 79–82 (1971).
Knowles et al., Journal of the Chem. Soc., Dec. 1960, 4885–4896.
Houlen-Weyl, *Methoden der Organischen Chemie*, X/I, Part 1, 4th Edition, pp. 483–484 (1971) (English translation).

*Primary Examiner*—Mary E. Ceperley
*Attorney, Agent, or Firm*—Bernard, Rothwell & Brown

[57] ABSTRACT

An improved nitric acid only nitration process wherein the improvement comprises adding an effective amount of a nitration promoting acid anhydride to the reaction mixture to enhance the rate of nitration.

16 Claims, No Drawings

NITRATION REACTIONS WITH ACID ANHYDRIDE PROMOTERS

This is a continuation of application Ser. No. 567,485, filed Jan. 1, 1984, now abandoned.

The present invention relates to an improved process for the nitration of aromatic compounds. Specifically, in a nitric acid only nitration process, the rate of nitration of aromatic compounds may be greatly enhanced by the addition of one or more acid anhydrides to the reaction mixture.

BACKGROUND

It is known to nitrate various aromatic compounds including, for example, phthalimides, phthalic acids, and phthalic anhydrides by treatment with a mixture of concentrated sulfuric acid and nitric acid. Specific teachings of these nitration reactions may be found in Takekoshi, U.S. Pat. No. 3,868,389; Bacha et al, U.S. Pat. No. 4,137,419; and Cook et al, U.S. Pat. Nos. 3,933,852, 3,981,933 and 3,887,588.

Recently, it was discovered that aromatic compounds could be nitrated in a nitration reaction which employed only nitric acid. Specifically, copending patent application Ser. No. 917,926 filed Oct. 10, 1986 and having an effective filing date of Dec. 8, 1983, assigned to the same assignee as the present invention, discloses the nitration of alkylphthalimides in at least 95% concentrated nitric acid. Related copending patent application Ser. No. 559,575 filed Dec. 8, 1983, now abandoned, also assigned to the same assignee as the present invention discloses the nitration of phthalic acids, phthalic anhydrides and derivatives thereof in a nitration process using only nitric acid. Both of these copending patent application teach the use of high temperatures in order to achieve the best rate of nitration, thus short nitration times. However, even at such high temperatures, for example above 50° C., the time for completion of the nitration, or substantially so, may be three hours or more.

It is an object of the present invention to substantially enhance the rate of nitration in the nitric acid only nitration process without elevating the temperature of the nitration reaction.

It is also an object of the present invention to provide a nitric acid only nitration process that may be used at lower temperatures without detrimentally affecting the rate of nitration.

SUMMARY

It has now been discovered that the rate of nitration of aromatic compounds in the all nitric acid only nitration process (i.e., one not employing sulfuric acid in addition to nitric acid) may be greatly enhanced by the addition of acid anhydrides to the reaction mixture. This method gives very fast rates of nitration compared to reactions without the addition of acid anhydrides, thus greatly shortening the batch time for the production of, for example, nitrophthalimides, nitrophthalic acids, or any other nitrated aromatic substrate in the nitric acid only nitration process. It also makes more viable a continuous system for the all nitric acid nitration process.

Specifically, the improved nitric acid only nitration process of the present invention comprises (1) forming a solution of the aromatic substrate in a solvent of nitric acid of at least about 95% by weight concentration, preferably at least about 97.5% by weight concentration, (2) reacting the mixture within a temperature range of from about $-20°$ C. to the boiling point of nitric acid, (3) allowing the reaction to run to produce the nitrated derivatives of the reactant substrate and (4) thereafter recovering the nitrated products by methods known in the art, wherein the improvement consists essentially of adding one or more acid anhydrides to the aforementioned solvent or solution to enhance the rate of nitration. The method of the present invention may also comprise the additional step of elevating the temperature of the reaction mix during or following nitration to reduce or destroy by-products, particularly dinitro by products, formed during nitration.

The present invention is most particularly applicable to the nitration of such aromatic compounds as phthalimides. Preferred acid anhydrides for use as catalysts in the method of the present invention are the inorganic and organic acid anhydrides, most preferably phosphoric anhydride, nitric anhydride, sulfur trioxide, acetic anhydride and trifluoroacetic anhydride, among others.

DETAILED DESCRIPTION

The process of the present invention provides for the nitration of aromatic substrates at a greatly enhanced rate in the nitric acid only nitration process. Specifically, the use of rate enhancing nitration promoters in the nitric acid only nitration process provides for greatly enhanced rates of nitration even at lower temperatures, with lower weight ratios of nitric acid to aromatic substrate, and with lower concentration nitric acids. As disclosed in the above-identified copending patent applications, the nitric acid only nitration process is one which does not require nor employ sulfuric acid in addition to nitric acid in order to conduct the nitration.

In general the improved nitric acid only nitration process of the present invention comprises (1) forming a solution of the aromatic substrate in a solvent of nitric acid and an effective amount of a rate enhancing acid anhydride nitration promoter, (2) reacting the mixture within a temperature range of from about $-20°$ C. to the boiling point of nitric acid, (3) allowing the nitration to run to produce the nitrated derivatives of the aromatic substrate and (4) thereafter recovering the nitrated products.

The nitric acids useful for the nitric acid only nitration process should have a concentration of at least about 95% by weight and is preferably within the range of from about 97.5 to about 100% concentration. Nitric acids of lower concentration may be used, however, their use results in processes which are too slow to be cost effective. Nitric acids of such concentration are available commercially or may be prepared by known concentrating methods from more widely available commercial nitric acid of 60 to 67% concentration.

The amount of concentrated nitric acid used should be at least of about the stoichiometric amount necessary to attach one nitro($NO_2$) group on the aromatic nucleus of the aromatic substrate. Generally, the mole ratio of nitric acid to the aromatic substrate should be from about 1 to about 20, preferably from about 1 to about 12, most preferably from about 1 to about 6. Obviously, lower or higher amounts of nitric acid may be used in the all nitric acid nitration process, however, lower amounts of nitric acid result in poor yields and too slow a reaction rate to be cost effective, whereas higher amounts of nitric acid may result in unnecessary spoiling of concentrated nitric acid and increased costs for such acid and its recycling.

The temperature at which the reaction should run should generally fall within the range of from about −20° C. to the boiling point of nitric acid, preferably from about 10° C. to about 70° C., most preferably from about 20° C. to about 60° C. More specifically the actual temperature to be employed is dependent upon the desired rate of reaction and, in part, the aromatic substrate and the desired nitration products. In general, the lower the temperature the slower the reaction and the greater the ratio of the 4-isomer to 3-isomer formed in the nitrated aromatic products. Conversely, with higher temperatures, the reaction rate is increased and the ratio of the 4-isomer to 3-isomer is smaller. Further, as disclosed by the aforementioned copending patent applications, aromatic substrates having a high propensity to nitrate, such as N-methyl phthalimide, do not require as high a reaction temperature as substrates having less propensity to nitrate, for example phthalic acid, in order to obtain a good rate of nitration.

For the purpose of this specification and the appended claims, the "boiling point of nitric acid" is defined as the temperature at which the specific nitric acid used, under the pressure employed, boils. This definition is necessitated by the fact that nitric acids of less than 100% concentration have a higher boiling point than 100% concentrated nitric acid and that the boiling point of nitric acid may be elevated by raising the pressure under which the reaction takes place above atmospheric. Such instances are clearly intended to be within full scope of the present invention as set forth in this specification and claimed by the appended claims.

It should also be noted that temperatures outside the range of temperatures disclosed above may be employed with the present process. However, lower temperatures result in a reaction rate which is too slow to be cost effective, whereas higher temperatures require operation at above atmospheric pressure to prevent boiling and subsequent loss of nitric acid.

Briefly, the pressure range under which this process operates may vary from vacuum to above atmospheric pressure. Depending on the type of reactor or reactors employed, they may preferentially operate under slight vacuum for process and safety reasons. Otherwise, the process is generally run at about atmospheric pressure.

The nitric acid only nitration process is generally applicable to the nitration of aromatic compounds, particularly the phthalimides, phthalic acids, phthalic anhydrides and derivatives thereof. Most preferably, the present invention relates to the improved nitric acid only nitration of N-substituted phthalimides, especially the N-alkyl phthalimides and their derivatives. Suitable N-alkyl phthalimides may be represented by the formula:

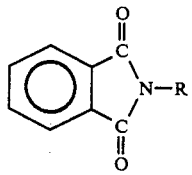

wherein R is a $C_1$ to $C_{10}$, preferably a $C_1$ to $C_4$, hydrocarbon. These may be prepared by effecting reaction between an alkylamine and phthalic anhydride, as taught by Markezich in U.S. Pat. No. 4,020,089, incorporated herein by reference. The N-alkyl phthalimide may be added to the reactor or solvent in any suitable form, e.g. powder, flake, etc. This process is particularly suitable for the nitration of N-alkyl phthalimide wherein the alkyl group is methyl, ethyl, n-propyl, i-propyl or n-butyl.

As taught by the aforementioned copending patent applications, the rate of reaction may be varied based on the weight ratio of reactants, the specific reactants and nitric acid used, and, most importantly, the temperature at which the nitration reaction is conducted. It has now been found that the rate of nitration may be greatly enhanced by adding to the reaction mix a nitration promoter. Preferred nitration promoters are organic and inorganic acid anhydrides. These are generally known compounds and available commercially.

Suitable organic acid anhydrides will generally be of the formula:

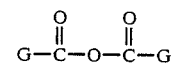

wherein each G is independently a substituted or non-substituted $C_1$ to $C_6$, preferably $C_1$ to $C_4$, alkyl group, or a substituted or non-substituted phenyl group. Substituted organic acid anhydrides are preferably substituted with halogens, especially fluorine. Especially preferred organic acid anhydrides are, for example, acetic anhydride and trifluoroacetic anhydride.

Likewise, most inorganic acid anhydrides will be suitable for use in the practice of the present invention. Exemplary of suitable inorganic acid anhydrides include for example boric anhydrides, phosphoric anhydride, chromic anhydride, nitric anhydride, sulfur trioxide and the like. Especially preferred are phosphoric anhydride, nitric anhydride and sulfur trioxide.

Generally, the acid anhydride, whether it be organic or inorganic, should be added to the reaction mixture in an effective amount sufficient to enhance the rate of nitration. While it is expected that smaller amounts will enhance the rate of nitration, it is preferred that the amount of acid anhydride promoters be from about 0.5 times to about 5 times the stoichiometric amount, preferably from about 0.8 to about 2 times the stoichiometric amount, based on the substrate to be nitrated. Most preferably, the amount of acid anhydride used should be of about the stoichiometric amount.

Of course it is to be understood that the effectiveness of certain acid anhydrides will vary depending upon the particular substrate to be nitrated and in certain limited instances are inoperable. (See e.g. copending U.S. patent application Ser. No. 170,708 filed Mar. 14, 1988, having an effective filing date of Jan. 3, 1984, now abandoned). However, it may be possible to predict the effectiveness of certain acid anhydrides by assessing their effectiveness with a particular substrate and then comparing that substrate's propensity to nitrate with the subsequent substrate to be nitrated. For example, it would be expected that all acid anhydrides that show rate enhancement for e.g. N-methylphthalimide would greatly enhance nitrations of other substrates whose propensity to nitration was equal to or greater than that of N-methylphthalimide.

The mode of mixing and the sequence of addition of reactants is not critical to the operability of the process of the present invention. For example, the acid anhydride promoter may be added to the nitric acid prior to, simultaneous with or following addition of the substrate to be nitrated. Additionally, any or all of the reactants may be premixed and then added to the reactor vessel. Again, whether the premix of any two reactants preceeds the addition of the third reactant is not important. It is also possible that any or all reactants or premixes be maintained at the desired reaction temperature, or any other temperature, prior to mixing or entering the reactor.

It is preferred, however, that the nitric acid or nitric acid substrate premix be cooled, preferably to about 0° C. prior to the addition of the nitration promoter and that such mixing takes place in the reactor vessel due to the high reactivity and, more importantly, to the extremely exothermic nature of such mixing. For example, addition of the promoter to nitric acid at room temperature causes immediate and excessive boiling of the nitric acid and may, especially at higher temperatures, result in an explosion.

Generally, the process of the present invention comprises mixing the aromatic substrate to be nitrated and the acid anhydride together with the concentrated nitric acid in a reactor or reactors preferably equipped with a stirrer or agitating means and means for heating and cooling the reactor. The reactor(s) may be such as to allow for either batch or continuous processing.

Specific variations in the design of the process systems employable to practice the present invention are known to those skilled in the art. For example, it is possible to use one or more reactors in series or in parallel which operate in the plug flow mode with or without radial mixing and with or without heating or cooling. Alternatively, it is possible to use one or more reactors in series or in parallel which operate in the back mixing mode, again with or without heating or cooling and operating in a batch or continuous mode. Finally, it is also possible to use a combination of reactors with features of both foregoing.

The nitration products prepared by the process of the present invention may be recovered from the reaction mix by any of the known methods for recovery of nitrated products. Exemplary of the methods available include: extraction; spray drying; precipitation and drying and the like. Recovered unreacted substrate may be reused and the spoiled or used nitric acid may be recycled by known methods for reuse.

The process of the present invention may be modified by the additional step of elevating the temperature of the reactor during or following nitration for a sufficient period of time to reduce or eliminate by-products, particularly dinitro by-products, formed during the nitration process. While essentially any increase in temperature will increase the destruction of such undesirable by-products, it is preferred that the temperature of the reactor be elevated to at least about 40° C., preferably from about 50° C. to about 60° C. Obviously, nitration reactions run at 50° C. or higher will inherently destroy some of the undesirable by-products, however, increasing the temperature even higher will enhance the destruction of said by-products and result in the production of essentially pure nitrated products.

In order that those skilled in the art may better understand how the present invention may be practiced, the following examples are given by way of illustration and not by way of limitation.

DESCRIPTION OF THE PREFERRED EMBODIMENTS

Generally, all reaction products were analyzed by High Pressure Liquid Chromotography (HPLC) wherein 50 $\mu$l aliquots of the reaction mix were quenched in 3.8 mls. of 0.96M sodium acetate and 0.05M tetraethylammonium bromide for the phthalic acid and phthalic anhydride reactions and 3.8 mls of a 1:1 mixture of an aqueous phase consisting of 0.005M tetraethylammonium bromide, 0.035M acetic acid, and 0.07M sodium acetate and acetonitrile.

The samples were analyzed on a Waters $\mu$ Bondpak/$C_{18}$ column, using a flow rate of 1.5 ml/min and a 280 nm detector. The mobile phase for the phthalic acid/anhydride determinations consisted of a solution of 0.005M tetraethyl-ammonium bromide, 0.035M acetic acid and 0.07M sodium acetate. The mobile phase for the alkylphthalimide determinations consisted of 70% of the above mobile phase and 30% of a 90:10 acetonitrile:methanol solution.

TABLE I

| | Enhanced Nitration of N-methyl Phthalimide | | | |
|---|---|---|---|---|
| | | % N-Methyl Phthalimide Remaining After Time | | |
| Nitration Promoter | Amount | 2 min. | 10 min. | 4-NPI/3-NPI |
| Phosphoric Anhydride ($P_2O_5$) | 1.25 | 88.5 | 28.1 | 19.6 |
| Sulfur Trioxide ($SO_3$) | 2.07 | 5.45 | .29 | 20.2 |
| Nitric Anhydride ($N_2O_5$) | 3.03 | 30.1 | 0 | 21.3 |
| Acetic Anhydride ($(CH_3CO)_2O$) | 2.69 | 55.2 | .79 | 20.5 |
| Trifluoro Acetic Anhydride ($(CF_3CO)_2O$) | 5.56 | 64.4 | .38 | 20.9 |
| Control | — | 97.4 | 87.3 | 21.1 |

EXPERIMENTAL 1

A series of nitric acid only nitration reactions were run demonstrating the effectiveness of various inorganic and organic acid anhydrides as nitration promoters. These examples and the specific nitration promoters were as shown in Table 1. Specifically, 15 parts by weight of 99% concentrated nitric acid was added to a reaction vessel along with a stirring means and cooled until the nitric acid began to freeze. The appropriate amount of acid anhydride, as shown in Table 1 was slowly added to the cooled nitric acid and the mixture was then allowed to come to the desired reaction temperature. To this stirred solution, 1.5 parts by weight of N-methyl phthalimide was added and the nitration reaction allowed to run at 25°–30° C. The result of these nitration reaction and the ratio of 4- to 3-nitro-N-alkylphthalimide formed are shown in Table 1.

As is clearly shown in Table 1, each of the acid anhydrides tested resulted in exceptional enhancement of the rate of nitration. Essentially, all of the N-methyl phthalimide was completely reacted within ten minutes at 25°–30° C., as opposed to only 13.6% in the control sample were no nitration promoter was used.

There was, however, some, although slight, variation in the effectiveness of the nitration promoters. For example, in the phosphoric anhydride promoted reaction, 28.1 mole percent of the N-methylphthalimide remained unreacted after ten minutes, however, this still anhydride and as such would likely promote the nitration of substrates even less active than phthalic anhydrides.

Table II also demonstrates the effectiveness of elevating the temperature of nitration on the rate. Comparison of the examples in which phthalic anhydride is nitrated at 40° C. and 70° C. with sulfur trioxide demonstrates the dramatic improvement in rate achieved by the use of both promoter and higher temperature. On the other hand, comparison of those examples wherein phosphoric anhydride is used demonstrates the ability to get great rate enhancement with lower amounts of nitration promoter at higher temperatures.

TABLE II

| Run | Substrate | Temperature °C. | Acid-Anhydrides Promoter | Amount (pts.) | % Substrate Remaining After Time (M.D.) % Substrate (Min.) | | |
|---|---|---|---|---|---|---|---|
| 1 | Phthalic Anhydride | 30–45 | Control | — | 98.3(10) | | 71.6(120) |
| 2 | Phthalic Anhydride | 30–45 | Nitric Anhydride ($N_2O_5$) | 1.6 | 98.6(10) | | 81.1(120) |
| 3 | Phthalic Anhydride | 40 | Control | — | 97.3(10) | 83.2(60) | 62.4(156) |
| 4 | Phthalic Anhydride | 40 | Phosphoric Anhydride $P_2O_5$ | 1.25 | 88.7(10) | 61.9(60) | 38.8(156) |
| 5 | Phthalic Anhydride | 40 | Sulfur Trioxide $SO_3$ | 2.07 | 67.4(10) | 3.96(60) | 0.49(156) |
| 6 | Phthalic Anhydride | 40 | Acetic Anhydride $(CH_3CO)_2O$ | 2.69 | 99.2(10) | 97.7(60) | 96.2(156) |
| 7 | Phthalic Anhydride | 40 | Trifluoroacetic Anhydride $(CF_3CO)_2O$ | 5.56 | 99.3(10) | — | 93.4(156) |
| 8 | Phthalic Anhydride | 70 | Control | — | 92.7(10) | 64.4(10) | 14.1(120) |
| 9 | Phthalic Anhydride | 70 | Phosphoric Anhydride | 0.87 | 82.0(5) | 46.5(30) | 7.70(120) |
| 10 | Phthalic Anhydride | 70 | Sulfur Trioxide | 2.07 | 7.98(5) | 1.96(15) | — |
| 11 | Phthalic Acid | 40 | Control | — | 92.7(10) | 81.2(60) | 63.8(156) |
| 12 | Phthalic Acid | 40 | Sulfur Trioxide | 2.07 | 39.0(10 | 1.14(60) | −0(156) |
| 13 | Phthalic Acid | 40 | Trifluoroacetic Anhydride | 5.56 | 98.5(10 | 96.2(60) | 92.2(156) | represented about a six fold increase over the control. Also, as is evident, certain nitration promoters are shown to start faster than others, yet the same end result of overall rate enhancement is achieved. Finally, it is to be noted that the use of any one acid anhydride nitration promoter had very little impact on the ratio of 4-nitro-N-methyl phthalimide to 3-nitro-N-alkyl phthalimide formed.

From these results it is expected that all of the acid anhydrides that show rate enhancement for N-methyl phthalimide would greatly enhance nitrations of other substrates whose propensity to nitration is equal to or greater than that of the phthalimide.

EXPERIMENTAL II

A series of all nitric acid nitration reactions were prepared as in Experimental 1, except that 1.5 parts of phthalic acid or phthalic anhydride, as set forth in Table 2, was substituted for N-methylphthalimide.

The results shown in Table II once again demonstrate the great enhancement in the rate of nitration achieved by the use of various acid anhydrides as nitration of aromatic compounds. However, these results also demonstrate selectivity of certain nitration promoters for certain substrates. Specifically, these examples demonstrate the efficiency of the inorganic acid anhydrides, especially phosphoric anhydride and sulfur trioxide, as opposed to the apparent inoperability of the organic acid anhydride promoters in the enhancement of nitration of phthalic anhydride and phthalic acid. Further, it is evident that certain operable acid anhydrides have a greater effect than others upon a particular substrate. In particular, it is clear that sulfur trioxide is especially effective for the nitration of phthalic acid and phthalic Obviously, other modifications and variations of the present invention are possible in light of the above teachings. It is, therefore, to be understood that changes may be made in the particular embodiments of the invention described which are within the full intended scope of the invention as defined by the appended claims.

I claim:

1. An improved process for the nitration of an N-($C_1$–$C_{10}$) alkyl phthalimide, which comprises (a) forming a solution of the N-($C_1$–$C_{10}$) alkyl phthalimide in a solvent of at least about 95% nitric acid, (b) allowing the solution to react at a temperature of from about −20° C. to about the boiling point of nitric acid to produce a nitrated N-($C_1$–$C_{10}$) alkyl phthalimide, and (3) recovering the nitrated N-($C_1$–$C_{10}$) alkyl phthalimide; wherein the improvement comprises adding a nitration-enhancing effective amount of a nitration-promoting acid anhydride to the reaction solution of step (a).

2. The process of claim 1 wherein the nitration promoting acid anhydride is present in an amount of from about 0.5 times to about 5.0 times the stoichiometric amount based on the N-($C_1$–$C_{10}$) alkyl phthalimide.

3. The process of claim 1 wherein the nitration promoting acid anhydride is present in an amount of from about 0.8 times to about 2 times the stoichiometric amount based on the N-($C_1$–$C_{10}$) alkyl phthalimide.

4. The process of claim 1 wherein the nitration promoting acid anhydride is present in about a stoichiometric amount based on the N-($C_1$–$C_{10}$) alkyl phthalimide.

5. The process of claim 1 wherein the nitration promoting acid anhydride is an inorganic acid anhydride selected from the group consisting essentially of nitric anhydride, phosphoric anhydride and sulfur trioxide.

6. The process of claim 1, wherein the nitration-promoting acid anhydride is an organic acid anhydride.

7. The process of claim 6, wherein the organic acid anhydride is represented by the formula:

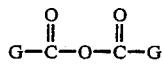

wherein each G is independently selected from the group consisting of $C_1$ to $C_6$ alkyl groups unsubstituted or substituted with one or more halogen atoms selected from the group consisting of fluorine, chlorine and bromine.

8. The process of claim 7 wherein the organic acid anhydride is selected from the group consisting of acetic anhydride and trifluoroacetic anhydride.

9. The process of claim 1 wherein the nitric acid is from about 97.5 to about 100% concentrated.

10. The process of claim 1 wherein the mixture is reacted at a temperature of from about 10° C. to about 70° C.

11. The process of claim 1 wherein the mixture is reacted at a temperature of from about 20° C. to about 60° C.

12. The process of claim 1 wherein the mole ratio of nitric acid to N-($C_1$–$C_{10}$) alkyl phthalimide is from about 1 to about 20.

13. The process of claim 1 wherein the mole ratio of nitric acid to N-($C_1$–$C_{10}$) alkyl phthalimide is from about 1 to about 12.

14. The process of claim 1 wherein the mole ratio of nitric acid to N-$C_1$–$C_{10}$) alkyl phthalimide is from about 1 to about 6.

15. The process of claim 1, wherein the N-($C_1$–$C_{10}$) alkyl phthalimide is an N-($C_1$–$C_4$) alkyl phthalimide.

16. The process of claim 1, wherein the N-($C_1$–$C_{10}$) alkyl phthalimide is N-methylphthalimide.

* * * * *